(12) United States Patent
Collins

(10) Patent No.: US 8,968,297 B2
(45) Date of Patent: Mar. 3, 2015

(54) MICROWAVE AND RF ABLATION SYSTEM AND RELATED METHOD FOR DYNAMIC IMPEDANCE MATCHING

(75) Inventor: George J. Collins, Fort Collins, CO (US)

(73) Assignee: Covidien LP, Mansfield, MA (US)

( * ) Notice: Subject to any disclaimer, the term of this patent is extended or adjusted under 35 U.S.C. 154(b) by 742 days.

(21) Appl. No.: 13/186,107

(22) Filed: Jul. 19, 2011

(65) Prior Publication Data

US 2013/0023871 A1    Jan. 24, 2013

(51) Int. Cl.
| | |
|---|---|
| A61B 18/12 | (2006.01) |
| A61B 18/14 | (2006.01) |
| A61B 18/00 | (2006.01) |
| A61B 18/16 | (2006.01) |

(52) U.S. Cl.
CPC .......... *A61B 18/1233* (2013.01); *A61B 18/1477* (2013.01); *A61B 2018/00577* (2013.01); *A61B 2018/00589* (2013.01); *A61B 2018/00595* (2013.01); *A61B 2018/0063* (2013.01); *A61B 2018/00708* (2013.01); *A61B 2018/00875* (2013.01); *A61B 2018/141* (2013.01); *A61B 2018/1412* (2013.01); *A61B 2018/167* (2013.01)
USPC ................................. 606/38; 606/34; 333/32

(58) Field of Classification Search
CPC ............... A61B 18/12; A61B 18/1206; A61B 18/1233; A61B 12/00642; A61B 12/00666; A61B 12/00755; A61B 12/00785
USPC .......................................... 606/32–52; 333/32
See application file for complete search history.

(56) References Cited

U.S. PATENT DOCUMENTS

| | | |
|---|---|---|
| D223,367 S | 4/1972 | Kountz |
| 4,204,549 A | 5/1980 | Paglione |
| D263,020 S | 2/1982 | Rau, III |
| D266,842 S | 11/1982 | Villers et al. |
| D278,306 S | 4/1985 | McIntosh |
| D295,893 S | 5/1988 | Sharkany et al. |
| D295,894 S | 5/1988 | Sharkany et al. |

(Continued)

FOREIGN PATENT DOCUMENTS

| | | |
|---|---|---|
| CN | 1103807 | 6/1995 |
| DE | 390937 | 3/1924 |

(Continued)

OTHER PUBLICATIONS

U.S. Appl. No. 08/136,098, filed Oct. 14, 1993, Roger A. Stern.

(Continued)

*Primary Examiner* — Jaymi Della
*Assistant Examiner* — Eunhwa Kim

(57) ABSTRACT

An electrosurgical system and method for performing electrosurgery is disclosed. The electrosurgical system includes an electrosurgical generator adapted to supply electrosurgical energy to tissue. The electrosurgical system includes an electrosurgical instrument, such as an electrosurgical antenna, knife, forceps, suction coagulator, or vessel sealer. The disclosed system includes an impedance sensor, a controller, dynamic impedance matching network, and an electrosurgical energy generator. The dynamic impedance matching network includes a PIN diode switching array configured to selectively activate a plurality of reactive elements. The disclosed arrangement of reactive elements provides real-time impedance correction over a wide range of impedance mismatch conditions.

20 Claims, 9 Drawing Sheets

(56) References Cited

U.S. PATENT DOCUMENTS

| | | | |
|---|---|---|---|
| 5,187,454 A * | 2/1993 | Collins et al. | 333/17.3 |
| 5,300,068 A * | 4/1994 | Rosar et al. | 606/34 |
| 5,323,778 A | 6/1994 | Kandarpa et al. | |
| 5,364,392 A | 11/1994 | Warner et al. | |
| D354,218 S | 1/1995 | Van de Peer | |
| 5,957,969 A | 9/1999 | Warner et al. | |
| 5,961,871 A | 10/1999 | Bible et al. | |
| D424,693 S | 5/2000 | Pruter | |
| D424,694 S | 5/2000 | Tetzlaff et al. | |
| D425,201 S | 5/2000 | Tetzlaff et al. | |
| 6,216,704 B1 | 4/2001 | Ingle et al. | |
| D449,886 S | 10/2001 | Tetzlaff et al. | |
| D457,958 S | 5/2002 | Dycus et al. | |
| D457,959 S | 5/2002 | Tetzlaff et al. | |
| 6,428,537 B1 | 8/2002 | Swanson et al. | |
| 6,629,974 B2 | 10/2003 | Penny et al. | |
| 6,670,864 B2 * | 12/2003 | Hyvonen et al. | 333/32 |
| D487,039 S | 2/2004 | Webster et al. | |
| 6,723,091 B2 | 4/2004 | Goble et al. | |
| 6,784,405 B2 | 8/2004 | Flugstad et al. | |
| D496,997 S | 10/2004 | Dycus et al. | |
| D499,181 S | 11/2004 | Dycus et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| 7,200,010 B2 | 4/2007 | Broman et al. | |
| D541,938 S | 5/2007 | Kerr et al | |
| 7,305,311 B2 | 12/2007 | van Zyl | |
| D564,662 S | 3/2008 | Moses et al. | |
| D576,932 S | 9/2008 | Strehler | |
| 7,513,896 B2 | 4/2009 | Orszulak | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| D634,010 S | 3/2011 | DeCarlo | |
| 7,927,328 B2 | 4/2011 | Orszulak et al. | |
| 2005/0283148 A1 * | 12/2005 | Janssen et al. | 606/34 |
| 2006/0160501 A1 * | 7/2006 | Mendolia et al. | 455/125 |
| 2007/0270924 A1 * | 11/2007 | McCann et al. | 607/99 |
| 2008/0015570 A1 | 1/2008 | Ormsby et al. | |
| 2009/0018536 A1 | 1/2009 | Behnke | |
| 2009/0076492 A1 * | 3/2009 | Behnke | 606/33 |
| 2009/0157073 A1 | 6/2009 | Orszulak | |
| 2009/0237169 A1 | 9/2009 | Orszulak | |
| 2009/0299360 A1 | 12/2009 | Ormsby | |
| 2010/0030107 A1 * | 2/2010 | Hancock | 600/567 |
| 2010/0076424 A1 | 3/2010 | Carr | |
| 2010/0079215 A1 | 4/2010 | Brannan et al. | |
| 2010/0082022 A1 | 4/2010 | Haley et al. | |
| 2010/0082023 A1 | 4/2010 | Brannan et al. | |
| 2010/0082024 A1 | 4/2010 | Brannan et al. | |
| 2010/0082025 A1 | 4/2010 | Brannan et al. | |
| 2010/0082083 A1 | 4/2010 | Brannan et al. | |
| 2010/0082084 A1 | 4/2010 | Brannan et al. | |
| 2010/0145328 A1 * | 6/2010 | Hancock et al. | 606/33 |
| 2011/0140607 A1 * | 6/2011 | Moore et al. | 315/111.21 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| GB | 2 434 872 | 8/2007 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001003776 | 1/2001 |
| JP | 2001008944 | 1/2001 |
| JP | 2001029356 | 2/2001 |
| JP | 2001037775 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO 00/48672 | 8/2000 |
| WO | WO 2004/047659 | 6/2004 |
| WO | WO 2005/115235 | 12/2005 |
| WO | WO 2007/055491 | 5/2007 |
| WO | WO 2008/043999 | 4/2008 |
| WO | WO 2008/044000 | 4/2008 |
| WO | WO 2008/044013 | 4/2008 |

(56) References Cited

FOREIGN PATENT DOCUMENTS

| WO | WO 2008/071914 | 6/2008 |
|---|---|---|
| WO | WO2008/110756 | 9/2008 |
| WO | WO2010/035831 | 4/2010 |

OTHER PUBLICATIONS

U.S. Appl. No. 08/483,742, filed Jun. 7, 1995, Roger A. Stern.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filled Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/113,736, filed May 23, 2011, Ladtkow et al.
U.S. Appl. No. 13/118,929, filed May 31, 2011, Bonn et al.
U.S. Appl. No. 13/206,075, filed Aug. 9, 2011, Lee et al.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.
U.S. Appl. No. 13/267,369, filed Oct. 6, 2011, Prakash et al.
U.S. Appl. No. 13/268,143, filed Oct. 7, 2011, Kenlyn S. Bonn.
U.S. Appl. No. 13/281,605, filed Oct. 26, 2011, Prakash et al.
U.S. Appl. No. 13/290,462, filed Nov. 7, 2011, Kenlyn S. Bonn.
U.S. Appl. No. 13/298,461, filed Nov. 17, 2011, Buysse et al.
U.S. Appl. No. 13/344,753, filed Jan. 6, 2012, Lee et al.
U.S. Appl. No. 13/343,788, filed Jan. 5, 2012, William O. Reid Jr.
U.S. Appl. No. 13/343,798, filed Jan. 5, 2012, William O. Reid Jr.
U.S. Appl. No. 13/344,790, filed Jan. 6, 2012, Lee et al.
U.S. Appl. No. 13/351,463, filed Jan. 17, 2012, Smith et al.
U.S. Appl. No. 13/351,553, filed Jan. 17, 2012, Mahajan et al.
U.S. Appl. No. 13/358,129, filed Jan. 25, 2012, Joseph D. Brannan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.

B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization." Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyms PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™ " Diseases of the Colon & Rectum, vol. 46, No. 1 , Jan. 2003.
Cosman et al., "Methods of Making Nervous System Lesions" in William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., Theoretical Aspects of "Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology. 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.

(56) References Cited

OTHER PUBLICATIONS

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non•Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs. N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating." NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York. 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.

(56) References Cited

OTHER PUBLICATIONS

T. Seki et al., (1994) "Ultrasonically Guided Percutaneous Microwave Coagulation Therapy for Small Hepatocellular Carcinoma," Cancer 74(3):817•825.
Urologix, Inc.-Medical Professionals: Targis™ Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'"Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns". JAMA, Aug. 16, 1971. vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.

(56) References Cited

OTHER PUBLICATIONS

European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 11004942 dated Sep. 23, 2011.
European Search Report EP 11174318.3 dated Nov. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.

\* cited by examiner

MICROWAVE AND RF ABLATION SYSTEM AND RELATED METHOD FOR DYNAMIC IMPEDANCE MATCHING

BACKGROUND

1. Technical Field

The present invention relates to systems and methods for performing a medical procedure, wherein the medical procedure includes transferring energy from an energy source to a patient via a transmission line and, more particularly, dynamically matching energy source impedance to tissue impedance.

2. Background of Related Art

Historically, surgery was performed using only mechanical tools, such as mechanical cutting instruments, scalpels, bladed forceps, saws, rongeurs, and the like. However, in recent years, technology has improved such that surgeons now frequently use electromagnetic waves to render a wider variety of surgical effects, e.g., by selectively modifying tissue using electromagnetic energy to produce a specific effect. The characteristics of the electromagnetic energy applied to tissue strongly correlates to the effect that the energy has on the tissue. These characteristics are therefore changed in accordance with the desired tissue effect. Two types of electromagnetic energy that are commonly applied during surgery include radiofrequency (RF) electrosurgical energy and microwave electrosurgical energy. During most medical procedures in which an energy source is employed, the energy generated for the medical procedure is transferred to a patient via a transmission line. One example of a medical procedure employing an energy source is an RF or microwave ablation surgical procedure. In an ablation surgical procedure the energy generated may be an RF or microwave surgical signal having a frequency and a wavelength associated therewith.

During the ablation surgical procedure, the surgical signal may be transmitted to the patient via a transmission line. Generally, the transmission line employed may have losses associated therewith that may be attributable to many factors. Factors that can cause transmission line losses include at least the following: the type of material used for the transmission line, the length of the transmission line, the thickness of the transmission line, and impedance mismatch between the transmission line and tissue load.

Generally, electrosurgery utilizes an electrosurgical generator, an active electrode and a return electrode. The electrosurgical generator generates electrosurgical energy typically above 100 kilohertz to avoid muscle and/or nerve stimulation between the active and return electrodes when applied to tissue. During electrosurgery, current generated by the electrosurgical generator is conducted through the patient's tissue disposed between the two electrodes. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The current causes the tissue to heat up as the electromagnetic wave overcomes the tissue's impedance. Although many other variables affect the total heating of the tissue, usually more current density directly correlates to increased heating.

Microwave surgical procedures invoke the application of microwave energy to tissue. Unlike low frequency RF therapy that heats tissue with current, microwave therapy heats tissue within the electromagnetic field delivered by an energy delivery device (e.g., a microwave antenna). Microwave surgical procedures typically utilize a microwave generator and an energy delivery device that delivers the microwave energy to the target tissue. One type of energy delivery device is a coaxial microwave antenna that forms an approximate dipole antenna. Microwave surgical systems involve applying microwave radiation to heat, ablate and/or coagulate tissue. For example, treatment of certain diseases requires destruction of malignant tissue growths (e.g., tumors) or surrounding tissue. It is known that tumor cells denature at elevated temperatures that are slightly lower than temperatures injurious to surrounding healthy cells. Therefore, by applying microwave energy to heat tumor cells to temperatures above 41° C. kills the tumor cells while adjacent healthy cells are maintained at lower temperatures avoiding irreversible cell damage. Another method used to treat diseased tissue is to resect a portion of the diseased organ, tissue or anatomical structure. For example, a liver may contain diseased tissue and healthy tissue. One treatment option is to pre-coagulate and ablate some of the liver tissue to facilitate resection of a portion of the liver including the diseased tissue. Microwave energy can be used during these types of procedures to pre-coagulate tissue prior to resection, to reduce bleeding during resection and to facilitate the actual resection of the tissue.

The microwave energy may be applied via an antenna that can penetrate tissue. There are several types of microwave antennas, such as monopole and dipole antennas. In monopole and dipole antennas, most of the microwave energy radiates perpendicularly away from the axis of the conductor. A monopole antenna includes a single, elongated conductor that transmits the microwave energy. A typical dipole antenna has two elongated conductors parallel to each other and positioned end-to-end relative to one another with an insulator placed therebetween. Each of the conductors is typically about ¼ of the length of the wavelength of the microwave energy making the aggregate length of both conductors about ½ of the wavelength of the microwave energy. Additionally, a microwave antenna may be adapted for use in a specific manner, for example, for endoscopic or laparoscopic (minimally invasive) procedures, for open procedures, and for percutaneous procedures.

It is known in the art that in order to maximize the amount of energy transferred from the source (microwave or RF generator) to the load (surgical implement or tissue), the line and load impedances should match. If the line and load impedances do not match (i.e. impedance mismatch) a reflected wave may be created. The ratio of the forward (primary) wave amplitude to the reflected wave amplitude is expressed as a reflection coefficient Γ. Standing waves within the transmission line may result from constructive and destructive interference between forward and reflected waves. The ratio between the wave maxima resulting from constructive interference and minima resulting from destructive interference is referred to as the voltage standing wave ratio, or VSWR. As an example, an unbalanced transmission line may exhibit an undesirably large VSWR up to around 4:1.

Standing waves created within the transmission line can contribute to the power loss associated with impedance mismatch, cause inaccurate energy dose (i.e., power) measurements, and impair monitoring of parameters associated with the surgical procedure. Moreover, standing waves may cause localized heating and failure of an interconnect (i.e., cable or coaxial cable), and cause premature wear and/or failure of the microwave or RF generator.

Further, during a typical ablation surgical procedure, the impedance at the surgical site changes over the course of the ablation procedure. This is because of tissue necrosis associated with the ablation surgical procedure. Generally, the energy source may include an impedance matching circuit and/or tuner, which may be configured to compensate for impedance changes at the surgical site.

Conventional impedance matching circuits may include devices such as motor-driven variable reactive elements, i.e., vacuum variable capacitors, and as a result may be large in size. In addition, because the energy source may have a much smaller wavelength than the length of the transmission line, it is often difficult to achieve accurate impedance matching in a rugged, reliable, and relatively compact design.

SUMMARY

A system and method for impedance matching during an electrosurgical medical procedure is disclosed. The disclosed system may employ an energy source, such as an electrosurgical generator, wherein the energy source may be connected to an energy delivering device via a transmission line. In one embodiment, the transmission line may be a coaxial cable. The disclosed system includes a dynamic impedance matching network having the capability to dynamically adjust to the varying load conditions. In embodiments, the dynamic impedance matching network is adapted to automatically adjust, or "self-tune", the energy delivery system to maintain a VSWR of less than about 1.5:1. It is envisioned that disclosed dynamic impedance matching network may have a relatively compact size, for example, occupying a printed circuit board (PCB) of less than about 30 cm². It is to be understood, however, that in embodiments, the disclosed dynamic impedance matching network may occupy a space less than, or greater than, about 30 cm². In embodiments, the PCB may be formed from any suitable material, for example without limitation, aluminum oxide ($Al_2O_3$). In embodiments, the electrosurgical generator is configured to generate an electrosurgical signal at a frequency in a range of about 915 mHz to about 925 mHz.

In one aspect of the present disclosure, a dynamic impedance matching network includes switchable reactive elements arranged in a pi configuration having a first shunt reactive leg, a series reactive leg, and a second shunt reactive leg. In embodiments the first shunt reactive leg includes a reactive element having a fixed value. The series reactive leg and the second shunt reactive leg each include a plurality of reactive elements arranged in a switchable configuration, such that the individual reactive elements contained therein may be selectively activated, separately or in combination, to achieve a desired (i.e., selectively variable) leg reactance. In embodiments, the reactive elements may include discrete components, such as without limitation surface mount capacitors (i.e., "chip caps"), inductive coils, tuned stubs formed on the PCB, capacitors formed on the PCB, and/or inductors formed on the PCB. In embodiments, a PCB capacitor may be formed by at least two adjacently disposed PCB traces (i.e., foil traces). A PCB capacitor constructed in this manner may be formed from traces disposed on the same side of the PCB or on traces formed on opposite side of the PCB. In embodiments, a PCB capacitor may have a dielectric portion that includes air and/or the PCB substrate.

An electrosurgical ablation system may be characterized by a range of antenna-to-tissue impedance values (i.e., impedance mismatches). The values of reactive elements in a dynamic impedance matching network of the present disclosure are selected accordingly to facilitate impedance matching over the range of mismatched values. Advantageously, the inventors have discovered that the identified range of mismatched antenna-to-tissue impedances can be corrected, i.e., effectively impedance matched, by the selective activation of four discrete values of series leg reactance and two discrete values of second shunt leg reactance. By this arrangement, sixty-four overlapping reactance ranges are available to dynamically impedance match the antenna to tissue. That is, the sixty-four overlapping ranges define an aggregate range of impedance matching ability which corresponds to the identified range of antenna-to-tissue impedance mismatch.

Each unique combination of reactive elements may be characterized by a circular region on a Smith diagram representing the reflection coefficient $\Gamma$ of the unique combination combination. The position of center point of the circular region on the Smith diagram is determined by the aggregate value of the series leg reactance and represents a zero reflection coefficient $\Gamma$ for the unique combination (i.e., perfect impedance matching). The diameter of the circular region represents the set of nominal reflection coefficient $\Gamma$ values which fall within an acceptable tolerance of reflection coefficient $\Gamma$, that is, the circle encloses those nominal reflection coefficient $\Gamma$ values which exhibit acceptable impedance matching. In embodiments, an acceptable reflection coefficient $\Gamma$ is less than about 0.15, which has been determined to correspond to a power transfer efficiency (i.e., match efficiency) of greater than about 96%.

In another aspect of the present disclosure, a PIN diode switch array is provided. The PIN diode array is configured to selectively activate at least one of the reactive elements. The PIN diode array is further configured dynamically activate/deactivate reactive elements ("hot switch") during application of electrosurgical energy. The PIN diode switch array may additionally or alternatively include field-effect transistor (PET) switching elements and/or microelectromechanical (MEMS) switching elements.

In yet another aspect, an electrosurgical system in accordance with the present disclosure includes a controller. The controller may be configured to receive any of a user input, an input related to impedance, a phase input, and/or a temperature input. The controller may further be configured to output any of a generator control signal, a PIN diode switch array control signal, and/or a user interface signal (i.e., a visual, audible, or haptic indicator). In embodiments, the controller includes a processor. For example without limitation, the controller may include a Cypress programmable system on a chip (PSOC), a PIC processor, a gate array or any suitable processor or chipset now or in the future known. The controller may be configured to execute a set of programmable instructions embodying a method of dynamically matching impedance as disclosed herein.

In still another aspect, an electrosurgical system in accordance with the present disclosure includes an RF measurement module configured to sense impedance and phase angle (i.e., phase shift) within the electrosurgical circuit. The RF Measurement module may include an Analog Device RFZ chip set configured to measure impedance and phase. The RF measurement module may be operatively coupled to at least one of the electrosurgical generator, the dynamic impedance matching network, and/or the electrosurgical antenna or electrode. The RF measurement module may also be configured to be in communication with the controller module and/or to provide impedance signals to the controller.

Also disclosed is a method of performing an electrosurgical procedure that includes the steps of providing an electrosurgical system that includes an electrosurgical instrument operatively coupled by a transmission line to an electrosurgical generator, a controller, an impedance sensor, a dynamic impedance matching network having includes a switchable reactive elements arranged in a pi configuration that includes a first shunt reactive leg, a series reactive leg, and a second shunt reactive leg, and a PINS diode array configured to selectively activate the reactive elements; applying the electrosurgical instrument to tissue; measuring the impedance of tissue; applying electrosurgical energy to tissue; and selectively activating at least one reactive element to match transmission line impedance to tissue impedance.

BRIEF DESCRIPTION OF THE DRAWINGS

The above and other aspects, features, and advantages of the present disclosure will become more apparent in light of the following detailed description when taken in conjunction with the accompanying drawings wherein.

DETAILED DESCRIPTION

Figure 1A:
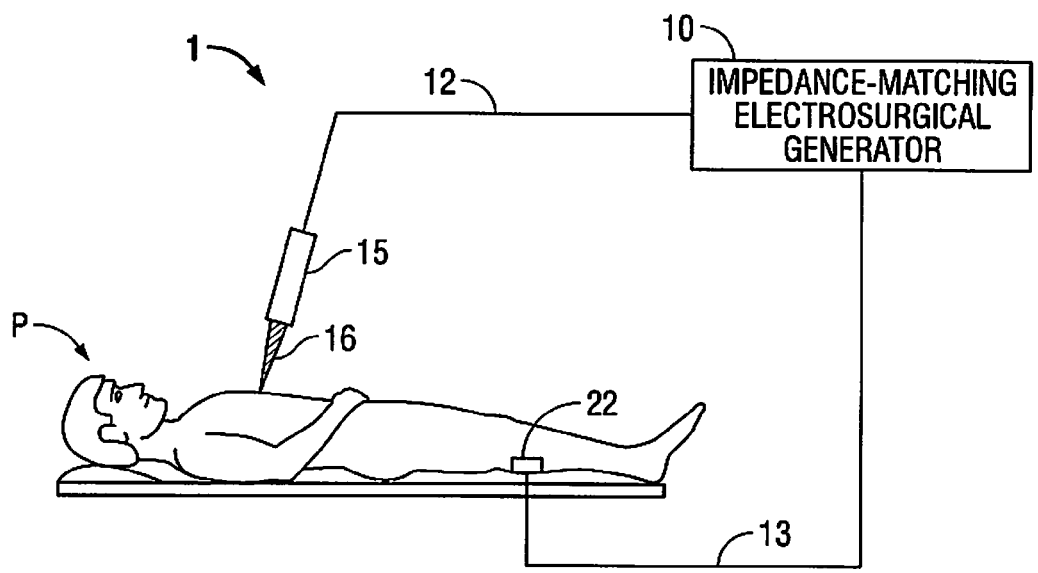
FIG. 1A illustrates an exemplary impedance-matching electrosurgical system according to the present disclosure operating in a monopolar mode.

Particular embodiments of the present disclosure will be described hereinbelow with reference to the accompanying drawings. In the following description, well-known functions or constructions are not described in detail to avoid obscuring the present disclosure in unnecessary detail. Those skilled in the art will understand that the present disclosure may be adapted for use with either an endoscopic instrument, laparoscopic instrument, or an open instrument. It should also be appreciated that different electrical and mechanical connections and other considerations may apply to each particular type of instrument, however, the novel aspects with respect to electrosurgical impedance matching are generally consistent with respect to both the open or endoscopic designs.

In the drawings and in the description which follows, the term "proximal" refers to the end of the instrument which is closer to the user (i.e., further from the patient), while the term "distal" refers to the end of the forceps which is further from the user (i.e., closer to the patient).

With reference to FIG. 1A, there is shown an embodiment of an impedance-matching electrosurgical system 1 in a monopolar configuration in accordance with the present disclosure. An impedance-matching electrosurgical generation 10 is operably coupled to an electrosurgical instrument 15 by a transmission line 12. Transmission line 12 may include a coaxial cable having a nominal impedance. In embodiments, transmission line 12 has a nominal impedance of about 50 ohms. Electrosurgical instrument 15 includes at least one electrode 16 configured to deliver electrosurgical energy to an operative site of patient P, i.e., to tissue. Electrode 16 is in electrical communication with transmission line 12 and to impedance-matching electrosurgical generator 10. Electrode 16 may be any suitable electrosurgical electrode, for example without limitation, a blade, a coagulator, a needle, an antenna, or a snare. Impedance-matching electrosurgical system 1 may additionally include an activation control (not explicitly shown), such as without limitation a handswitch included in the electrosurgical instrument 15 (not explicitly shown) or a footswitch (not explicitly shown). A return electrode 22 that is operably coupled to impedance-matching electrosurgical generator 10 by return conductor 13 is affixed to patient P. In use, return electrode 22 provides a return path for monopolar electrosurgical energy delivered by electrode 16.

Figure 1B:
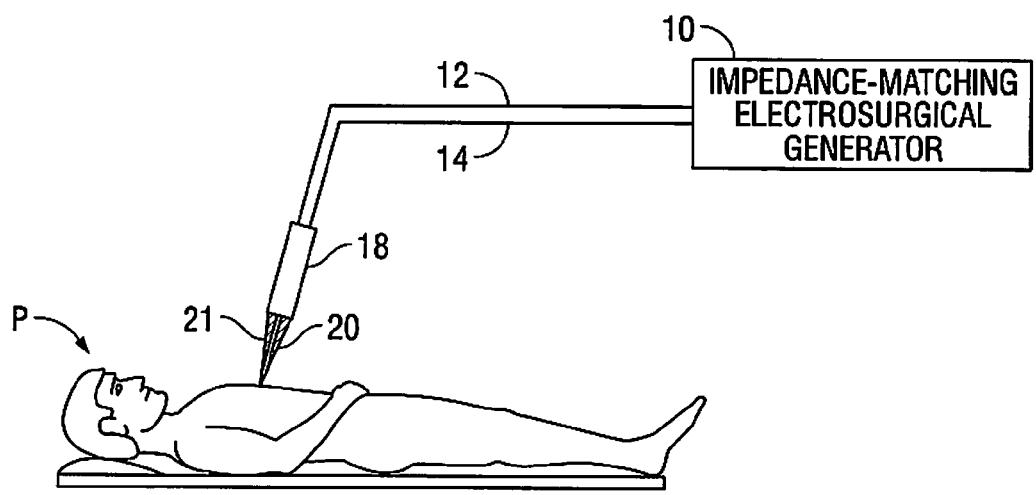
FIG. 1B illustrates an exemplary impedance-matching electrosurgical system according to the present disclosure operating in a bipolar mode.

Turning to FIG. 1B, an embodiment of an impedance-matching electrosurgical system 1 in accordance with the present disclosure in a biopolar configuration is illustrated. An impedance-matching electrosurgical generator 10 is operably coupled to an electrosurgical instrument 18 by transmission lines 12, 14. In embodiments, transmission lines 12, 145 may be included in a cable, i.e., a coaxial, twin-axial, and/or biaxial cable having a nominal impedance. In embodiments, transmission lines 12, 14 have a nominal impedance of about 50 ohms. Electrosurgical instrument 18 includes a bipolar electrode having two elements 20, 21 configured to apply electrosurgical energy in a bipolar mode to an operative site of patient P, i.e., to tissue. Bipolar electrode elements 20, 21 are in electrical communication with transmission lines 12, 14, respectively, and to impedance-matching electrosurgical generator 10. Bipolar electrodes 20, 21 may be any suitable electrosurgical electrode, for example without limitation, forceps, jaws, bypass cutters, anvil cutters, scissors, or a vessel sealer. Impedance-matching electrosurgical system 1 may additionally include an activation control (not explicitly shown), such as without limitation a handswitch included in the electrosurgical instrument 18 (not explicitly shown) or a footswitch (not explicitly shown).

Figure 2:
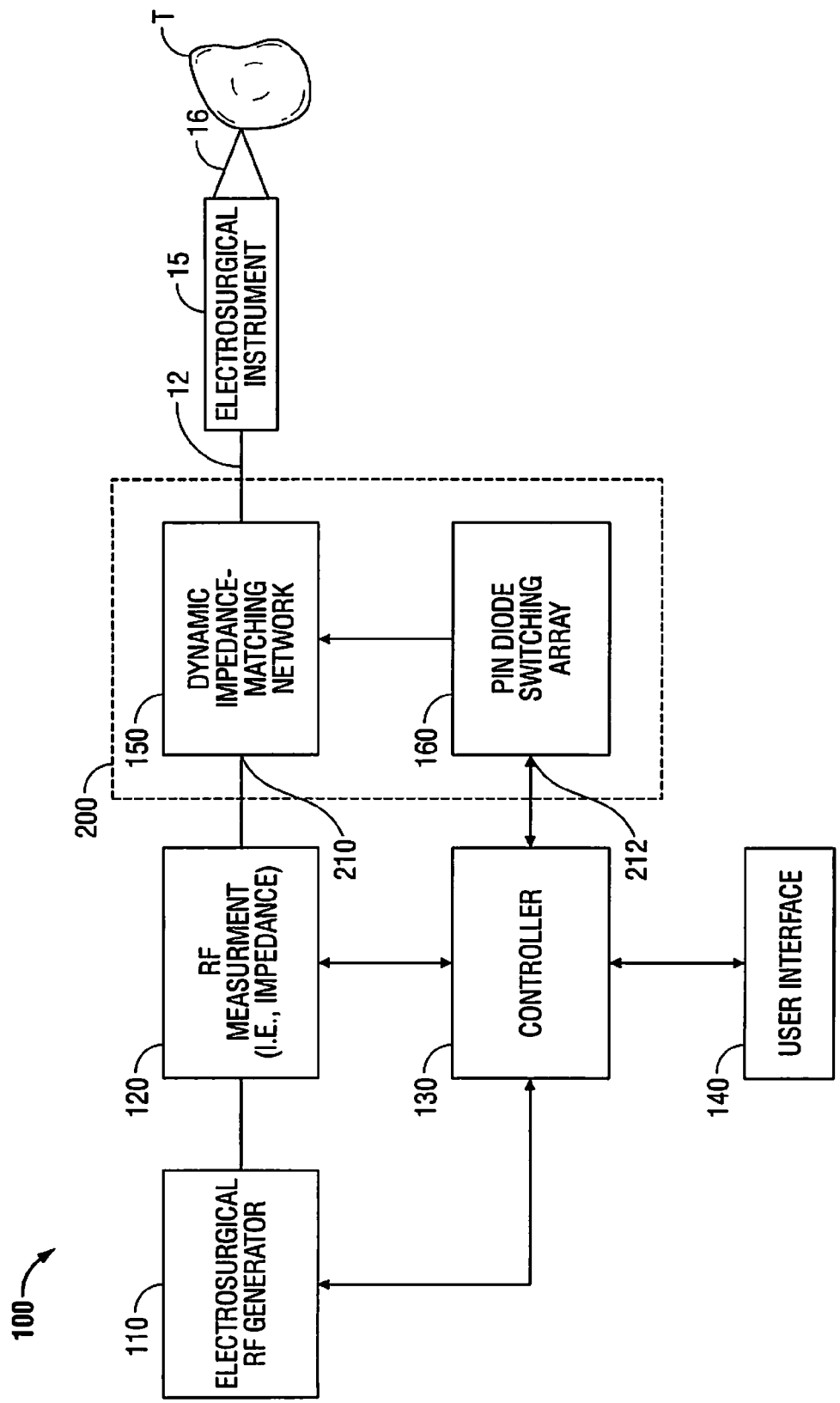
FIG. 2 illustrates a block diagram of an embodiment of an impedance-matching electrosurgical system according to the present disclosure.

A block diagram of an impedance-matching electrosurgical system 100 in accordance with the present disclosure will now be described with reference to FIG. 2. The impedance-matching electrosurgical system 100 includes an electrosurgical RF generator 110 configured to selectively provide electrosurgical energy. In embodiments, electrosurgical RF generator 110 is configured to output an RF signal in a frequency range of about 915 mHz to 925 mHz. It is to be understood, however, that a RF signal encompassing an additional or alternative frequency or frequency range is envisioned within the scope of the present disclosure. The RF output of electrosurgical RF generator 110 is in electrical communication with RF measurement module 120 that is configured to sense a characteristic of the electrosurgical signal. For example without limitation, RF measurement module 120 may be configured to sense the impedance, reflectance, SWR, voltage, current, and/or power of the electrosurgical signal. In embodiments, RF measurement module 120 may include an integrated circuit, such as without limitation, an Analog Devices AD8302 RF/IF Gain and Phase Detector.

Impedance-matching electrosurgical system 100 includes a controller 130 that is in operable communication with RF measurement module 120, RF generator 110, PIN diode switching array 160, and user interface module 140. Impedance-matching electrosurgical system 100 may be embodied in any of hardware, software, software in execution, firmware, microcode, bytecode, in virtualization, in a hardware description language, logic gates, circuitry, digital circuitry, RAM, ROM, MEMS, and the like. User interface 140 receives user input and provides the user input to controller 130. Controller 130 interprets the user input and controls operation of electrosurgical generation 110 in accordance therewith.

More particularly, controller 130 is configured to control RF generator 110 and PIN diode switching array 160. In particular, RF generator 110 generates sinusoidal waveforms of electrosurgical energy. RF generator 110 can generate a plurality of waveforms having various duty cycles, peak voltages, crest factors and other suitable parameters. Certain types of waveforms are suitable for specific electrosurgical modes. For instance, RF generator 110 generates a 100% duty cycle sinusoidal waveform in cut mode, which is best suited for ablating, fusing and dissecting tissue, and a 1-25% duty cycle waveform in coagulation mode, which is best used for cauterizing tissue to stop bleeding.

Controller 130 may include a microprocessor (not explicitly shown) operably connected to a memory (not explicitly shown) which may be volatile type memory (e.g., RAM) and/or non-volatile type memory (e.g., flash media, disk media, etc.). Controller 130 includes an output port that is operably connected to RF generator 110 that allows controller 130 to control the output of RF generator 110 according to either open and/or closed control loop schemes, and/or user input. Controller 130 may include any suitable logic processor (e.g., control circuit), hardware, software, firmware, or any other logic control adapted to perform the features discussed herein.

Impedance-matching electrosurgical system 100 includes an RF measurement module 120, and also includes an interface to at least one sensor (not explicitly shown) that is configured to measure a variety of tissue and energy properties (e.g., tissue impedance, output current and/or voltage, etc.) and to provide feedback to controller 130 in accordance with the measured properties.

RF measurement module 120 is operative communication with controller 130. The communication may be continuous or intermittent. The data may be communicated in analog form, digital form, using a pulse width modulated signal, using a frequency or analog modulated signal, or any other communication technology. Controller 130 is programmed to at least process data to control the generation and impedance matching of the electrosurgical energy.

Electrosurgical instrument 15 has one or more active electrodes 16 for treating tissue T of patient P. As described herein, electrosurgical instrument 15 may be any type of electrosurgical instrument (e.g., monopolar or bipolar) and may include active electrodes designed for a wide variety of electrosurgical procedures (e.g., electrosurgical cutting, ablation, etc.). Electrosurgical energy is supplied to electrosurgical instrument 15 by impedance-matching electrosurgical system 100 via transmission line 12, which is connected to an active output terminal, allowing electrosurgical instrument 15 to coagulate, ablate, and/or otherwise treat tissue endogenically. When impedance-matching electrosurgical system 100 is operated in a bipolar mode, the electrosurgical energy is returned to impedance-matching electrosurgical system 100 through a return pad 22 via cable 13 after passing through patient P.

The user interface 140 may include input controls, such as without limitation, buttons, activators, switches, touch screen, and the like (not explicitly shown) for controlling impedance-matching electrosurgical system 100. Input controls may be include a handswitch disposed on the instrument 15, a footswitch (not explicitly shown), or a control provided on the impedance-matching electrosurgical generator 10 (i.e., a "front-panel" control). Additionally or alternatively, user interface 140 may include one or more visual indicators and/or display screens (not explicitly shown) for providing the user with variety of output information (e.g., intensity settings, treatment complete indicators, etc.). The user interface 140 allows the user (e.g., a surgeon, nurse, or technician) to adjust the electrosurgical energy parameters (e.g., power, waveform, duty cycle, voltage, current, frequency, and/or other parameters) to achieve the desired electrosurgical energy characteristics suitable for a particular task (e.g., coagulating, tissue sealing, intensity setting, etc.). Additionally or alternatively, user interface 140 may include a settable desired tissue effect (e.g., hemostasis, coagulation, ablation, dissection, cutting, and/or to sealing tissue). The electrosurgical instrument 15 may also include one or more input controls (not explicitly shown) that may be redundant with user interface 140 of electrosurgical generator 10.

Figure 3:
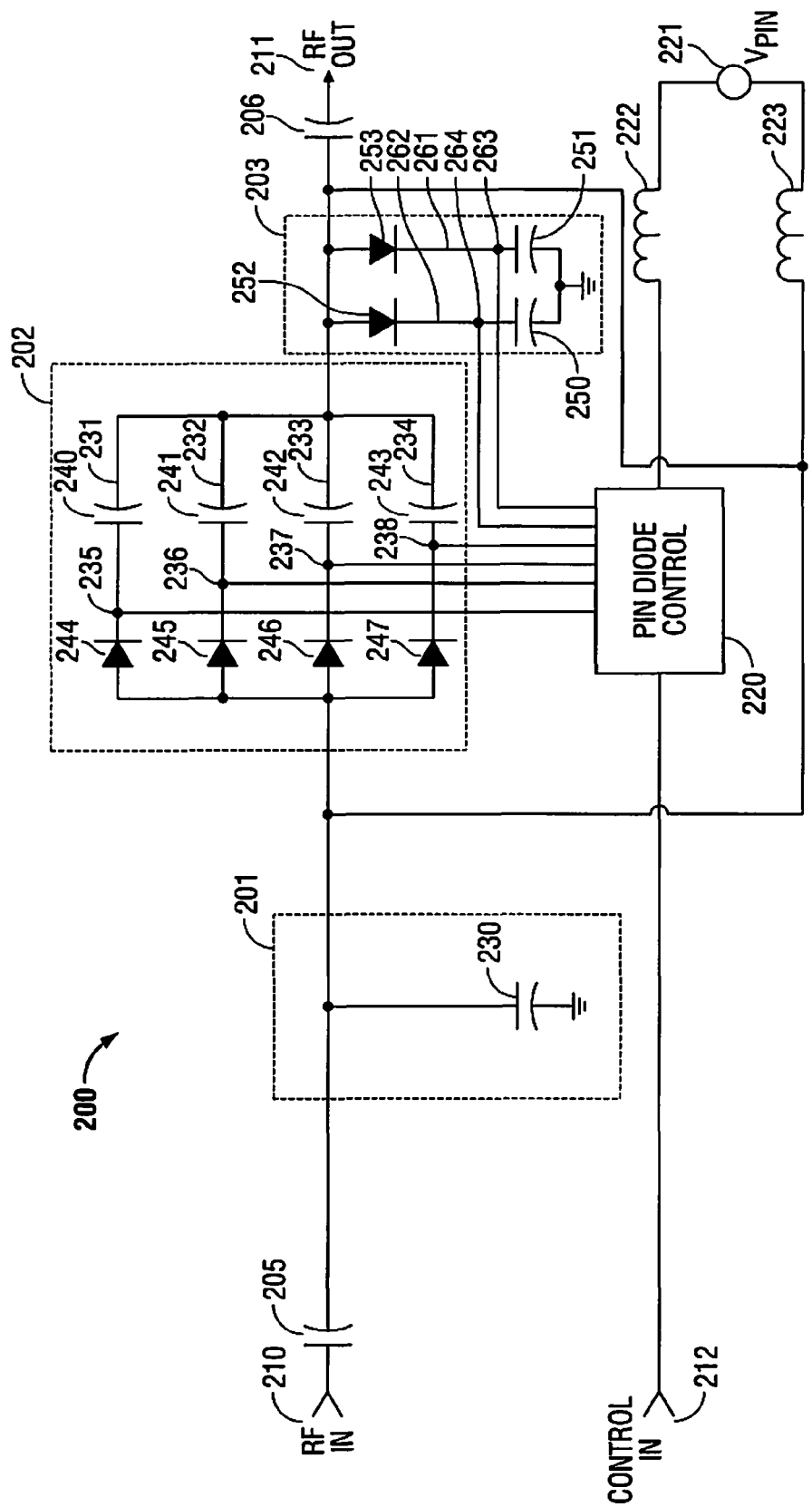
FIG. 3 is a circuit diagram of an embodiment of an dynamic impedance-matching module in accordance with the present disclosure.

Impedance-matching electrosurgical system 100 includes an impedance matching module 200 that includes a dynamic impedance matching network 150 and a PIN diode switching array 160. As shown in FIG. 3, impedance matching module 200 includes an input 210, an output 211, a fixed reactive shunt section 201, a variable reactive series section 202, and a variable reactive shunt section 203. Reactive sections 201, 202, and 203 are arranged in a pi configuration. Input isolation capacitor 205 and output isolation capacitor 206 are coupled in series with input 210 and output 211, respectively, to block DC current flow into or out of the RF signal path. In embodiments, input isolation capacitor 205 and output isolation capacitor 206 may have a value of about 1 nF.

In embodiments, fixed reactive shunt section 201 may include a fixed reactive element 230, which may be a capacitor, an inductor, or a combination thereof. Variable reactive series section 202 includes a plurality of reactive legs 231, 232, 233, 234 coupled in parallel, each reactive leg 231, 232, 233, 234 having a PIN diode coupled in series with a reactive element, i.e., PIN diodes 244, 245, 246, 247 are coupled in series with reactive elements 240, 241, 242, and 243, respectively. The common junction 235, 236, 237, 237 of each PIN diode 244, 245, 246, and reactive element 240, 241, 242, and 243 are operably coupled to PIN diode control module 220. PIN diode control module is configured to selectively bias any of PIN diodes 244, 245, 246, 247 in accordance with a control signal received at control input 212.

Variable reactive shunt section 203 includes a plurality of reactive legs 261, 262 coupled in parallel, each reactive leg 261, 262 having a PIN diode coupled in series with a reactive element, i.e., PIN diodes 252, 253 are coupled in series with reactive elements 250, 251, respectively. A common junction 263, 264 of each PIN diode 252, 253 and reactive element 250, 251 are operably coupled to PIN diode control module 220 that is configured to selectively bias any of PIN diodes 252, 253 in accordance with a control signal received at control input 212.

Under forward bias, a PIN diode (i.e., PIN diodes 244, 245, 246, 247, 252, 253) acts as a low resistance (short circuit) path that causes the corresponding reactive element 235, 236, 237, 237, 250, 251 to be switched in-circuit (i.e. activated). Conversely, under reverse bias, a PIN diode (i.e., PIN diodes 244, 245, 246, 247, 252, 253) acts as a high impedance (open circuit) path that causes the corresponding reactive element 235, 236, 237, 237, 250, 251 to be switched out of the circuit (i.e. deactivated).

DC bias source 221 provides bias current to PIN diode control module 220 that is configured to selectively apply bias to a PIN diode (i.e., PIN diodes 244, 245, 246, 247, 252, 253) as previously described. DC bias source 221 is isolated from the RF signal path by isolation inductors 222, 223. Isolation capacitors 205, 206 also provide DC isolation as previously described herein. PIN diode control module may include an integrated circuit, such as an Impellimax Decoded Five Channel −100V PIN Diode Driver or a Supertex HV3922 PIN Diode Driver −220V.

In embodiments, the values of the reactance elements 235, 236, 237, 237, 250, 251 are selected in accordance with binary encoding. For example without limitation, an embodiment in accordance with the present disclosure may include reactive legs 231, 232, 233, 234 having an impedance (Z) corresponding to 5Ω, 10Ω, 20Ω, and 40Ω, respectively. In this manner, the reactive series section 202 is configured to provide sixteen discrete values of reactance, i.e., from zero to 75Ω in 5Ω increments. Variable reactive shunt section 203 includes reactive legs 261, 262 that are configured to provide four discrete values. For example without limitation, reactive legs 261, 262 may have an impedance (Z) corresponding to 375Ω and 750Ω, respectively. In embodiments, controller 130 includes a look-up table for determining which reactive elements to activate to achieve the required impedance correction.

Figure 4:
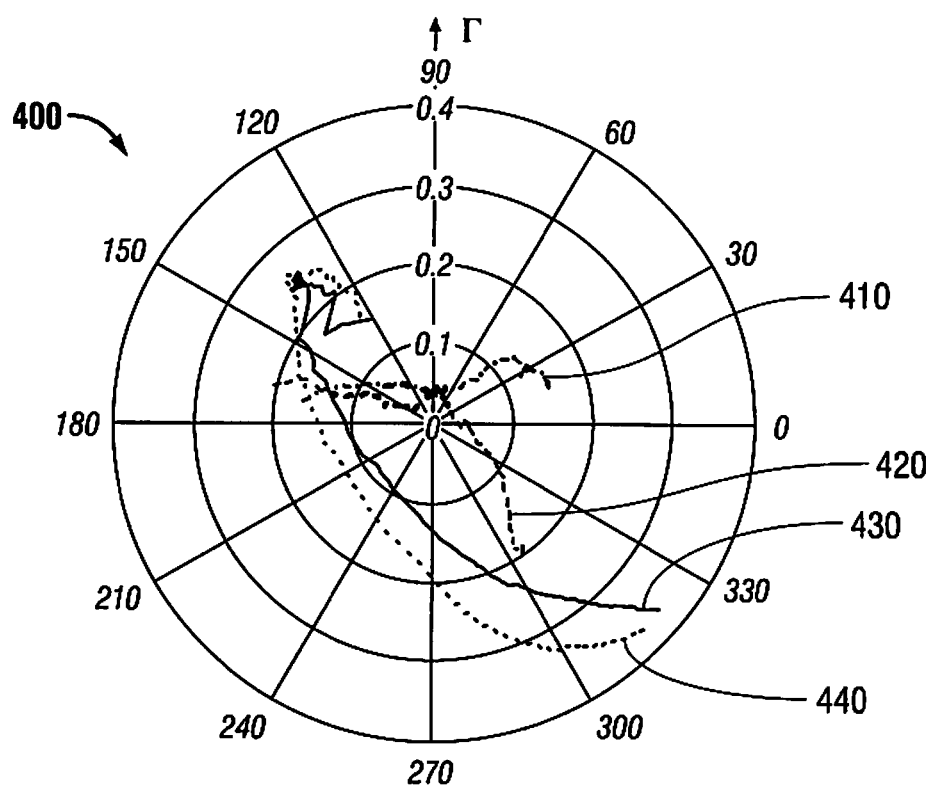
FIG. 4 is a Smith diagram illustrating relationships between reflection coefficient and impedance load.

The inventors have discovered relationships between reflection coefficient and impedance load which is best illustrated with reference to the Smith diagram 400 of FIG. 4. In particular, reflection coefficients of two exemplary electrosurgical antenna types are diagrammed against load impedance varied over a range of less than nominal generator impedance (i.e., less than about 50Ω) to greater than nominal generator impedance (i.e., greater than about 50Ω). For example, the reflection coefficient of a surgical antenna is shown by plots 430 and 440. The reflection coefficient of a percutaneous antenna is shown by plots 410 and 420. The plots reveal that the measured impedance mismatches, as plotted by the reflection coefficient data presented therein, are distributed in relatively narrow "bands." The required impedance matching range, i.e., tuning range of a dynamic impedance matching network, is thus greatly reduced. Correcting the impedance mismatch such that a corrected reflection coefficient is in a range of about zero to less than about 0.10, or in a range of about zero to less than about 0.15, yields a power transfer efficiency of greater than about 96%. A power transfer efficiency of greater than about 96% is considered to be within the acceptable operating range for an electrosurgical system.

Figure 5A:
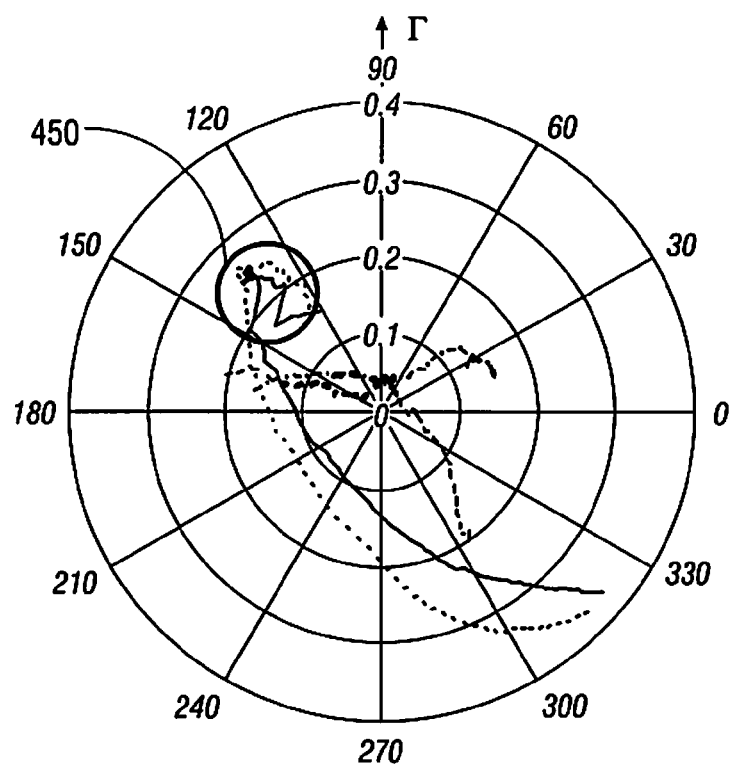
FIGS. 5A-5J are Smith diagrams illustrating relationships between reflection coefficient, impedance load, and impedance correction.
Figure 5B:
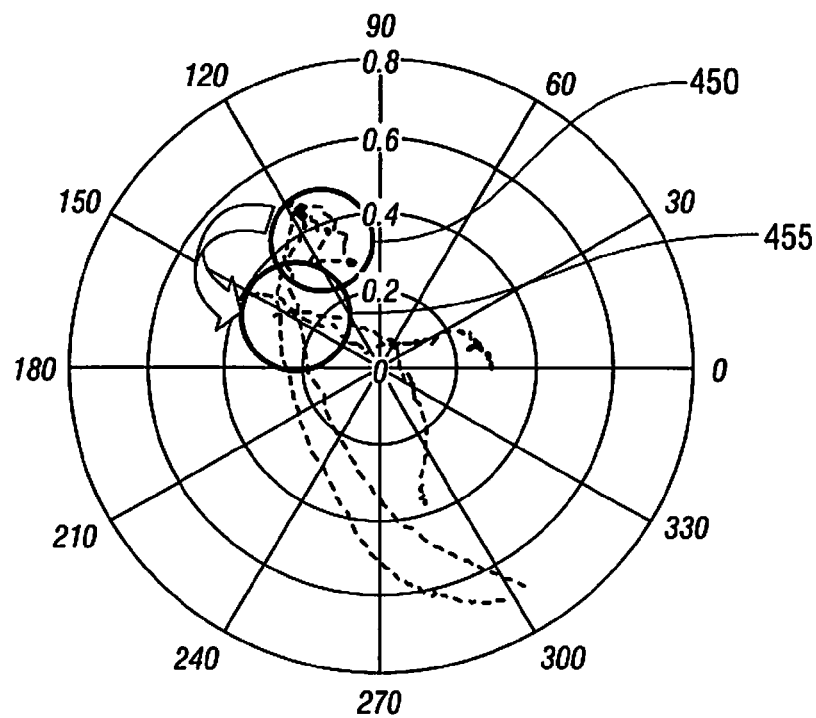
Figure 5C:
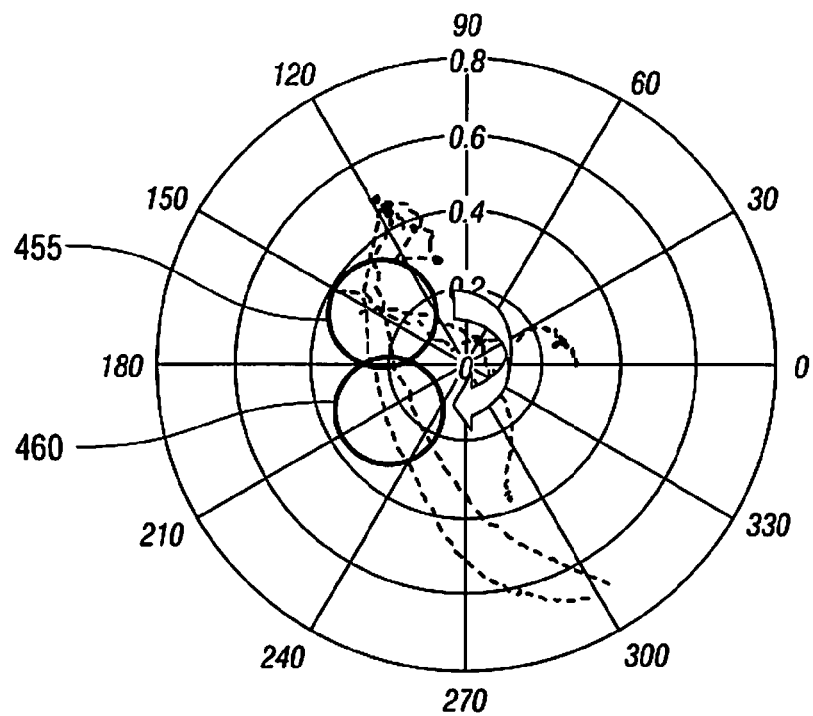
Figure 5D:
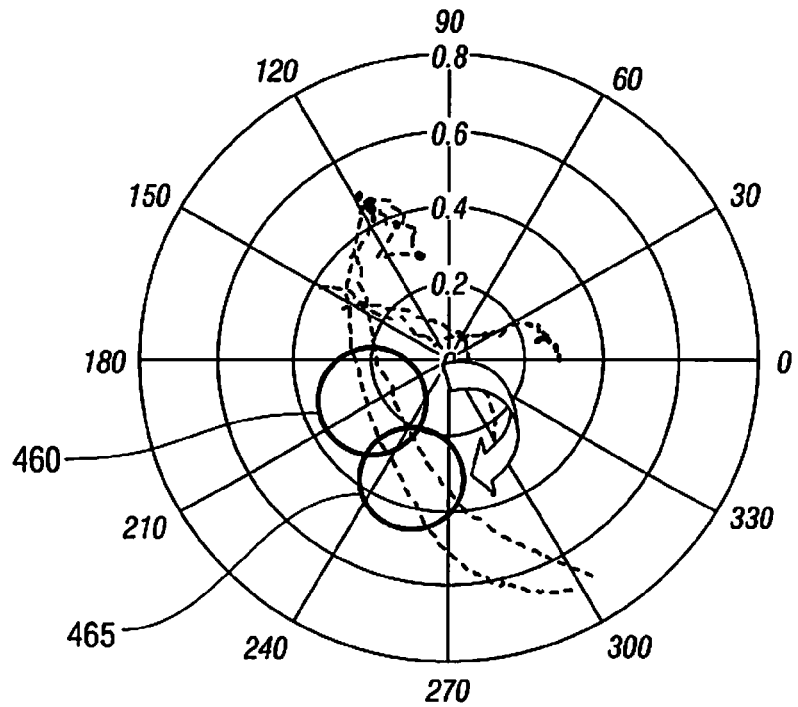
Figure 5E:
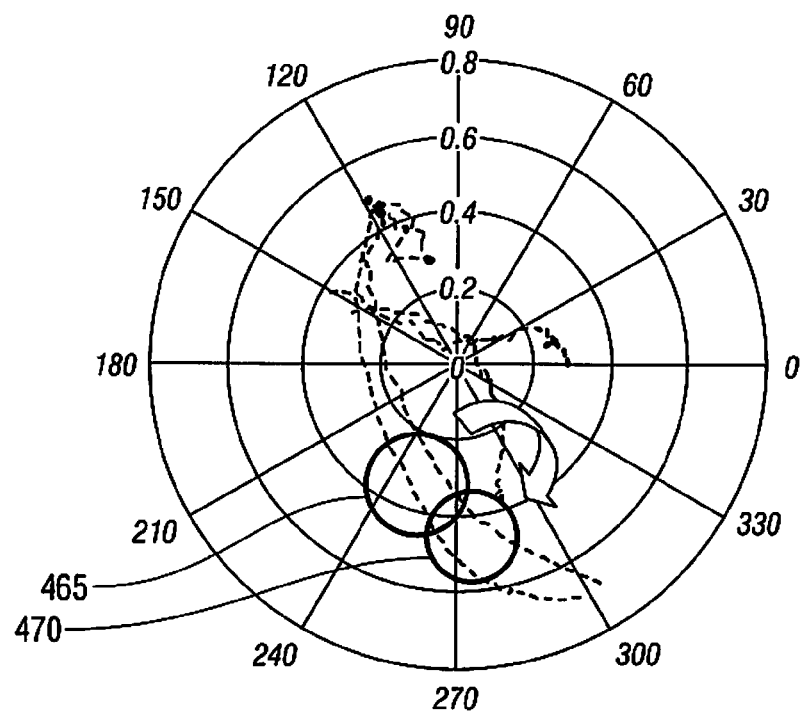
Figure 5F:
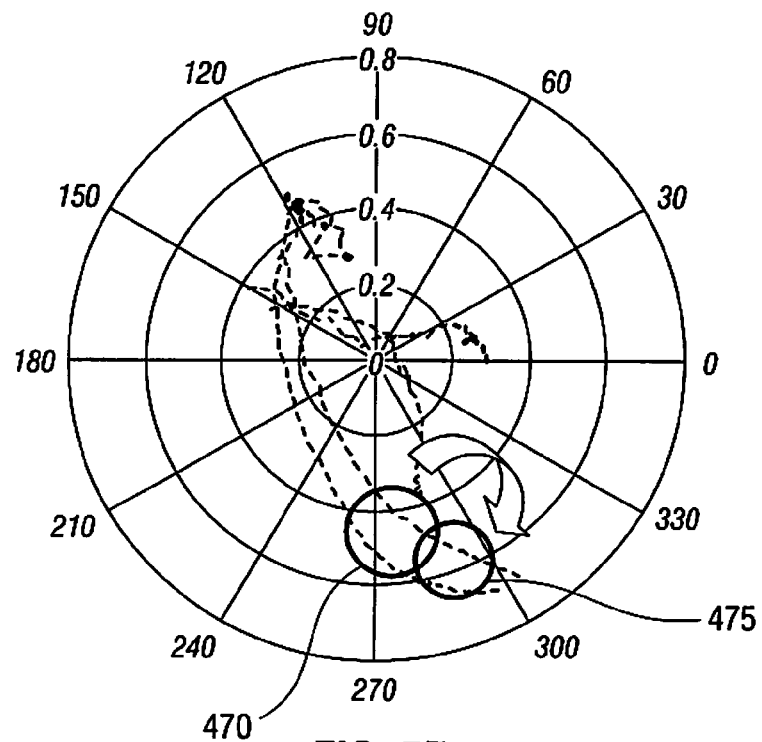
Figure 5G:
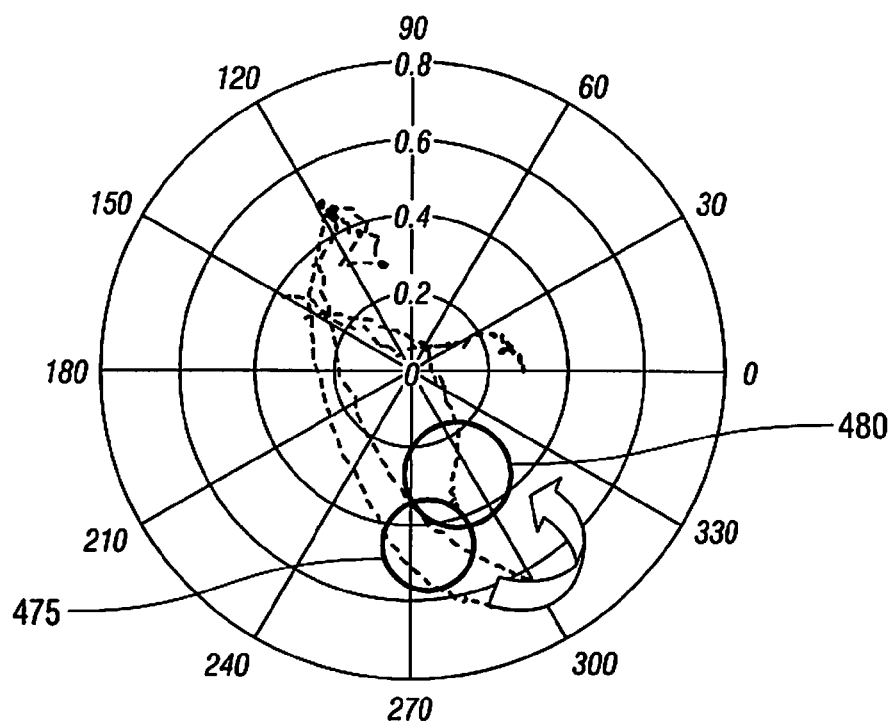
Figure 5H:
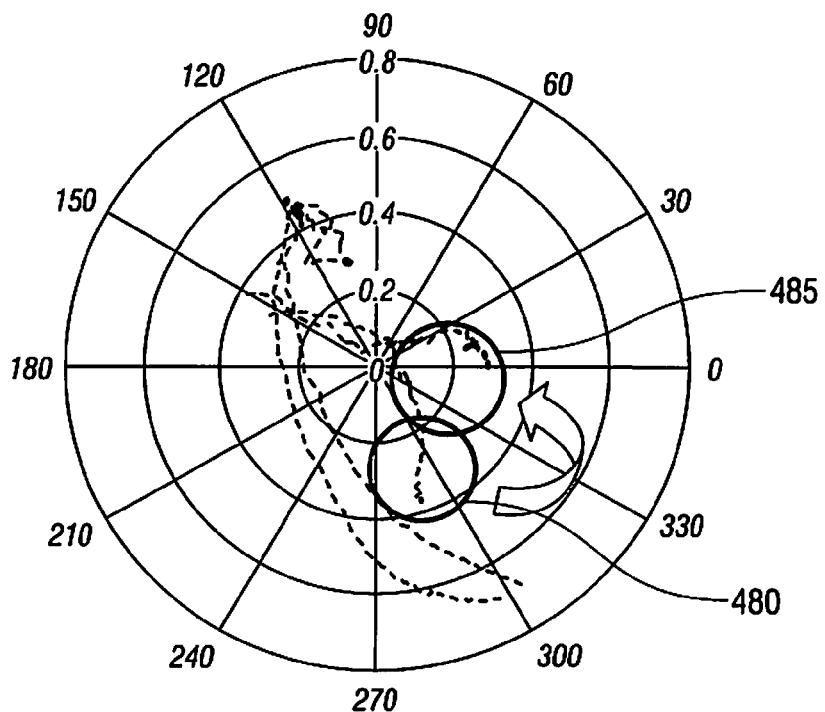
Figure 5I:
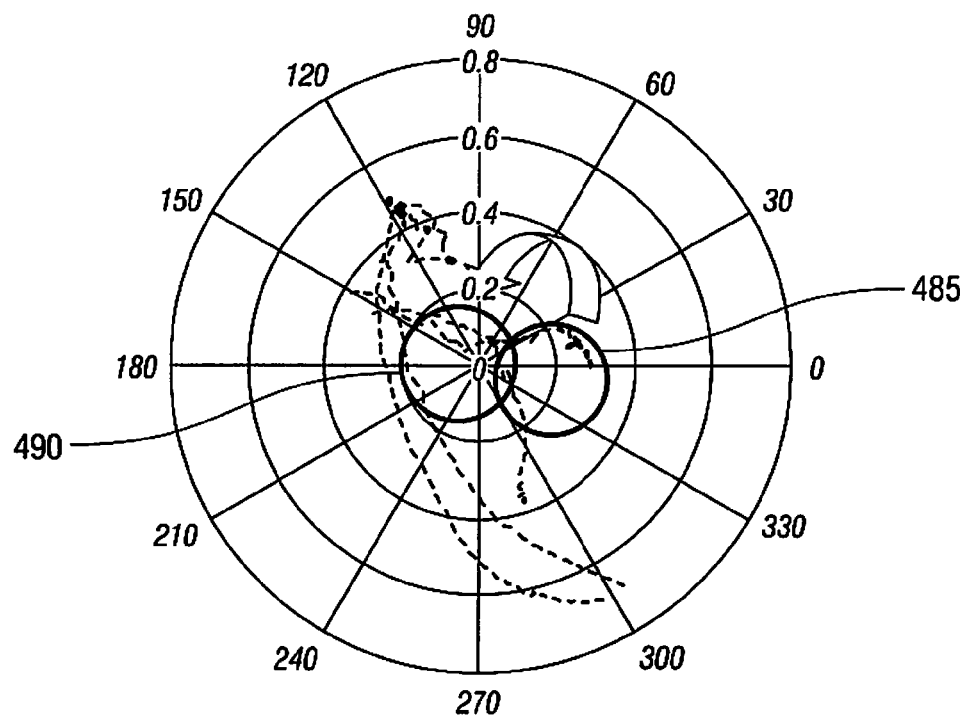
Figure 5J:
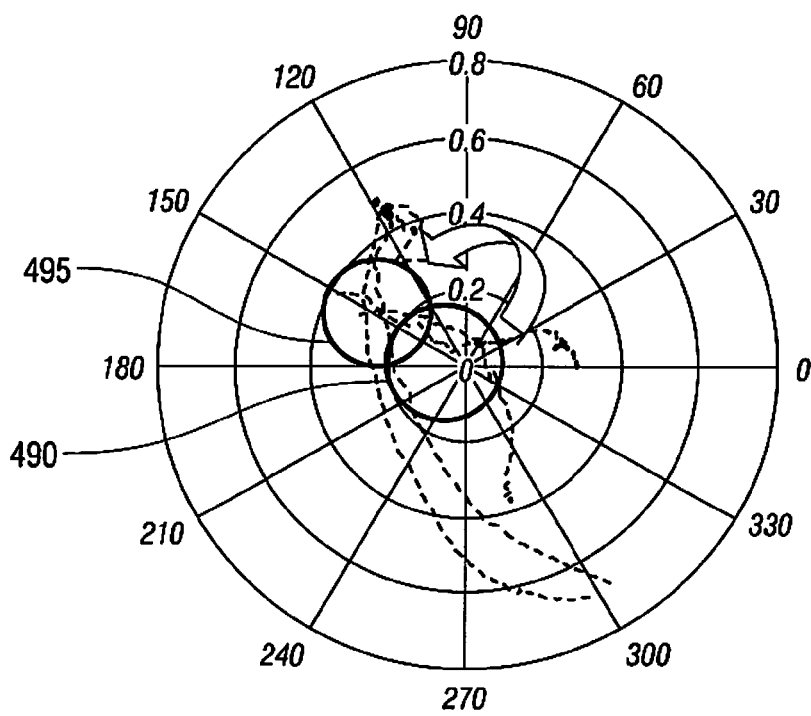

With reference now to FIG. 5A, a circular corrective region 450 encloses the set of data points representing reflection coefficients falling within about less than 0.15 of the nominal, i.e., center point, of circular corrective region 450. In accordance with the present disclosure, the location and diameter of circular corrective region 450 is determined by the corresponding values of reactive elements 201, 202, and 203. That is, the position and diameter of circular corrective region 450 is determined by the value of fixed reactance element 230, the aggregate value of reactive legs 231, 232, 233, and 234 of variable reactive series section 202, and the aggregate value of reactive legs 261 and 262 of variable reactive shunt section 203. As previously described, in embodiments of the presently disclosed system, sixty-four overlapping reactance ranges are available to dynamically impedance match the antenna to tissue. These overlapping ranges correspond to a series of overlapping circular corrective regions 450-495 as exemplified in FIGS. 5A-5J. The diameter and position of circular corrective regions 450-495 is dependent upon the selected aggregate reactance of the dynamic impedance matching network as described herein.

In an aspect of the present disclosure, a method of matching impedance includes the steps of measuring the impedance, identifying a corrective region in which the measured impedance falls, determining a combination of reactive elements corresponding to the identified corrective region, and activating the combination of reactive elements to match the measured impedance.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system, comprising:
a controller configured to:
   store a plurality of pre-determined corrective regions each including a plurality of impedance values and corresponding to a combination of reactive elements;
   receive an impedance measurement signal;
   identify a pre-determined corrective region encompassing the impedance measurement signal from the plurality of pre-determined corrective regions; and
   output an impedance matching control signal in response to the predetermined corrective region;
an impedance measurement module configured to sense an impedance of an electrosurgical transmission line, wherein the impedance measurement module is in operable communication with the controller;
a dynamic impedance-matching network configured to receive the impedance matching control signal, wherein the dynamic impedance-matching network includes:
   a plurality of reactive elements switchably coupled to the electrosurgical transmission line; and
   a switching array comprising switching elements configured to selectively switch at least one of the plurality of reactive elements in accordance with the impedance matching control signal;
an electrosurgical generator configured to generate an electrosurgical signal;
an electrosurgical instrument operably coupled to the electrosurgical generator via the electrosurgical transmission line.

2. The electrosurgical system according to claim 1, wherein the dynamic impedance-matching network further comprises a source of biasing energy.

3. The electrosurgical system according to claim 2, wherein the source of biasing energy is selected from a group consisting of a current source and a voltage source.

4. The electrosurgical system according to claim 1, wherein the plurality of reactive elements is selected from a group consisting of a capacitor and an inductor.

5. The electrosurgical system according to claim 1, wherein the dynamic impedance-matching network includes a printed circuit board formed at least in part of aluminum oxide.

6. The electrosurgical system according to claim 1, wherein each of the plurality of reactive element includes a value and the value of each of the plurality of reactive elements is selected in accordance with binary encoding.

7. The electrosurgical system according to claim 1, wherein the plurality of reactive elements are arranged in a pi configuration.

8. The electrosurgical system according to claim 7, wherein the pi configuration includes a first shunt reactive leg, a series reactive leg, and a second shunt reactive leg.

9. The electrosurgical system according to claim 8, wherein the first shunt reactive leg includes a fixed reactance, the series reactive leg includes a variable reactance, and the second shunt reactive leg includes a variable reactance.

10. The electrosurgical system according to claim 1, wherein the switching elements are selected from the group consisting of a PIN diode, a field-effect transistor, and a micromechanical switch.

11. The electrosurgical system according to claim 1, wherein the controller includes a processor.

12. The electrosurgical system according to claim 11, wherein the processor is configured to execute a set of the programmable instructions for performing impedance matching, the instructions including:
   measuring the impedance measurement signal;
   identifying a pre-determined corrective region from the plurality of stored pre-determined corrective regions in which the impedance measurement signal falls; and
   activating the plurality of reactive elements corresponding to the pre-determined corrective region in accordance with the impedance measurement signal.

13. An electrosurgical generator, comprising:
   a controller configured to:
      store a plurality of pre-determined corrective regions each including a plurality of impedance values and corresponding to a combination of reactive elements;
      receive an impedance measurement signal;
      identify a pre-determined corrective region encompassing the impedance measurement signal from the plurality of stored pre-determined corrective regions; and
      output an impedance matching control signal in response to the predetermined corrective region;
   an impedance measurement module configured to sense an impedance of an electrosurgical transmission line, wherein the impedance measurement module is in operable communication with the controller; and
   a dynamic impedance-matching network configured to receive the impedance matching control signal, wherein the dynamic impedance-matching network includes:
      a plurality of reactive elements switchably coupled to the electrosurgical transmission line; and
      a switching array comprising switching elements configured to selectively switch at least one of the plurality of reactive elements in accordance with the impedance matching control signal.

14. The electrosurgical system according to claim 13, wherein the dynamic impedance-matching network further comprises a source of biasing energy.

15. The electrosurgical system according to claim 14, wherein source of biasing energy is selected from a group consisting of a current source and a voltage source.

16. The electrosurgical system according to claim 13, wherein the plurality of reactive elements is selected from a group consisting of a capacitor and an inductor.

17. The electrosurgical system according to claim 13, wherein the dynamic impedance-matching network includes a printed circuit board formed at least in part of aluminum oxide.

18. The electrosurgical system according to claim 13, wherein each of the plurality of reactive elements includes a value and the value of each of said plurality of reactive elements are is selected in accordance with binary encoding.

19. The electrosurgical system according to claim 13, wherein the plurality of reactive elements are arranged in a pi configuration having a first shunt reactive leg, a series reactive leg, and a second shunt reactive leg, wherein the first shunt reactive leg comprises a fixed reactance, the series reactive leg comprises a variable reactance, and the second shunt reactive leg comprises a variable reactance.

20. The electrosurgical system according to claim 13, wherein the switching elements are consisting of a PIN diode, a field-effect transistor, and a micromechanical switch.

\* \* \* \* \*